United States Patent [19]

Zey et al.

[11] 4,076,727

[45] Feb. 28, 1978

[54] CYCLIC ACETAL ACRYLATES OR METHACRYLATES AND PROCESSES FOR PREPARING SAME

[75] Inventors: Edward G. Zey, Corpus Christi, Tex.; William A. Hoffmann, III, North Bergen, N.J.

[73] Assignee: Celanese Corporation, New York, N.Y.

[21] Appl. No.: 650,214

[22] Filed: Jan. 19, 1976

[51] Int. Cl.² .......................................... C07D 319/04
[52] U.S. Cl. ............................. 260/340.7; 260/340.9 R
[58] Field of Search .......................... 260/340.9, 340.7

[56] References Cited

U.S. PATENT DOCUMENTS

| | | | |
|---|---|---|---|
| 2,680,735 | 6/1954 | Fegley et al. | 260/340.9 X |
| 3,267,084 | 8/1966 | Rankin et al. | 260/340.7 X |
| 3,271,377 | 9/1966 | Mantell et al. | 260/340.7 X |
| 3,488,335 | 1/1970 | Braun | 260/340.9 R |

OTHER PUBLICATIONS

Hill et al., Journ. Amer. Chem. Soc., pp. 2242–2249, (1928).
Boekelheide et al., Journ. Amer. Chem. Soc., 3303–3307, (1949).

*Primary Examiner*—Ethel G. Love

[57] ABSTRACT

A process for preparing a new composition of matter useful in protective coatings having the general formulae:

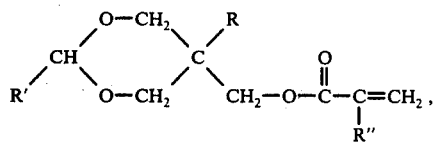

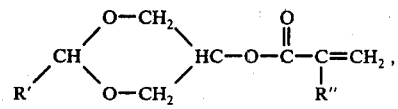

or 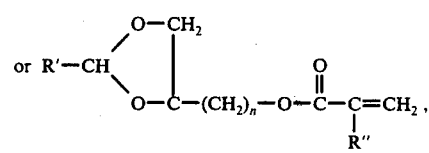

wherein R is —CH$_3$ or —CH$_2$—CH$_3$, R' is hydrogen, C$_1$–C$_3$ alkyl or C$_1$–C$_3$ halogenated alkyl, R" is hydrogen or methyl and n is 1–4. This composition is prepared by reacting the corresponding polyol with an aldehyde having the general formula

R'CHO wherein R' is hydrogen, C$_1$–C$_3$ alkyl or C$_1$–C$_3$ halogenated alkyl, and esterifying the resulting cyclic alcohol with acrylic or methacrylic acid.

5 Claims, No Drawings

CYCLIC ACETAL ACRYLATES OR METHACRYLATES AND PROCESSES FOR PREPARING SAME

BACKGROUND OF INVENTION

This invention relates to new compositions of matter. More particularly, this invention relates to processes for preparing new compositions of matter.

U.S. Pat. No. 3,530,167 discloses certain acetal-type polymers. However, the particular acetals utilized in the instant invention are not disclosed.

The *Journal of Radiation Curing*, July, 1975, discloses certain novel photosensitive monomers and polymers which are of the heterocyclic type, as does U.S. Pat. No. 3,759,942, to Himics.

The *Journal of Polymer Chemistry*, Part A-1, Vol. 5, pp. 287–306, 1967, discloses certain dioxolane-containing materials which are based upon a reaction between a polyol and a ketone. U.S. Pat. No. 3,271,311, to Mantell, et al, discloses certain compounds where the ester group is attached to a different carbon atom than are the ester groups disclosed in the instant invention.

Thus, it is an object of this invention to prepare new compositions of matter.

It is another object of this invention to discover new processes for preparing these new compositions of matter.

These and other objectives are obtained by preparing the compositions according to the process of the instant invention.

SUMMARY OF INVENTION

Basically, the instant invention involves the discovery of certain new compositions of matter and processes for preparing same. The new compositions of matter are represented by the general formulae:

$$R'-CH\diagup_{O-CH_2}^{O-CH_2}\diagdown C\diagup_{CH_2O-C-C=CH_2}^{R} \quad (1)$$
$$\phantom{R'-CH\diagup_{O-CH_2}^{O-CH_2}\diagdown C\diagup_{CH_2O-C-C=CH_2}^{R}}\phantom{xxx}\|\phantom{xxx}|$$
$$\phantom{R'-CH\diagup_{O-CH_2}^{O-CH_2}\diagdown C\diagup_{CH_2O-C-C=CH_2}^{R}}\phantom{xxxxx}O\phantom{xx}R''$$

$$R'-CH\diagup_{O-CH}^{O-CH_2}\diagdown HC-O-C-C\,CH_2 \quad (2)$$

or $$R'-CH\diagup_{O-CH-(CH_2)_n-O-C-C=CH_2}^{O-CH_2} \quad (3)$$

wherein R is —CH$_3$ or —CH$_2$CH$_3$, R' is hydrogen, C$_1$–C$_3$ alkyl or C$_1$–C$_3$ halogenated alkyl, R'' is hydrogen or methyl and n is 1–4. When trimethylolpropane or trimethylolethane is employed, products of the formula 1 type are produced. When glycerin or glycerin derivatives is used, a mixture of the formula 2 and 3 products is formed.

The process for preparing these compositions basically involves forming the cyclic alcohol by coreacting polyols selected from the group consisting of glycerin, trimethylolpropane, and trimethylolethane, with an aldehyde selected from formaldehyde (formalin) or any of the C$_2$–C$_4$ aldehydes or halogenated aldehydes, including butyraldehyde and formaldehyde, and coreacting the alcohol with acrylic or methacrylic acid.

DESCRIPTION OF INVENTION

As set out above, the instant invention involves a process for preparing certain novel compositions. These compositions are useful as reactive monomers in preparing coating compositions, plastic films, fibers, plastic castings, and the like. In addition, they are particularly useful as diluents in various unsaturated systems, particularly, ultraviolet curable coating compositions.

The first step in carrying out the reactions of the instant invention involves coreacting an aldehyde selected from the group consisting of formaldehyde and the C$_2$–C$_4$ aldehydes or halogenated aldehydes with a tri-alcohol selected from the group consisting of trimethylolpropane, trimethylolethane, and a glycerin derivative having the formula $$HOCH_2-CH(CH_2)_n-OH$$
$$\phantom{HOCH_2-CH}|$$
$$\phantom{HOCH_2-C}OH$$

wherein n is 1–4. The aldehyde is preferably formaldehyde, butyraldehyde or chloral. Where formaldehyde is used, it is preferably employed in the form of its aqueous formalin solution. The aldehyde and the triol are mixed essentially in equimolar ratios in the presence of an acid catalyst, such as hydrochloric acid, methane sulfonic acid, paratoluene sulfonic acid, and the like, in a reflux solvent. The reflux solvent should be of a rather low boiling point, preferably below about 100° C. Examples of the reflux solvents include benzene, toluene and xylene.

The initial reaction proceeds according to the following general reaction formula and is carried out at temperatures ranging up to about 150° C., preferably up to about 100° C.

$$R'CHO + CH_3-CH_2C(CH_2OH)_3 \xrightarrow{H+}$$

$$R'-CH\diagup_{O-CH_2}^{O-CH_2}\diagdown C\diagup_{CH_2-OH}^{CH_2-CH_3} + H_2O$$

As the reaction progresses, water of reaction is removed and the reaction is deemed complete when the theoretical water is removed.

The resulting product should preferably be purified by conventional chemical purification methods, including washing, extraction, distillation, evaporation, and the like. The product after purification is liquid and may be utilized as is for further reaction to form the acrylate or methacrylate ester.

While it would normally be thought that the cyclic acetal ring would be broken during a direct esterification reaction, it has surprisingly been found that, for example, the cyclic formal alcohol can be directly esterified with acrylic acid without any disruption of the cyclic formal ring. The esterification may be carried out with or without esterification catalysts. Examples of these catalysts include the previously mentioned acidic catalysts, such as paratoluene sulfonic acid, methane sulfonic acid, and the various acid catalysts, as well as preferably ion exchange esterification catalysts, such as divinyl benzene-styrene sulfonic acid reaction products.

In carrying out the esterification reaction, a mild polymerization inhibitor is preferably utilized. Examples of such materials include the quinones, such as hydroquinone and its monomethyl ether, the various phenols, p-tert-butylcatechol, p-methoxyphenol, 2,4-dichloro-6-nitrophenol, n-propyl gallate, di-tert-butyl-p-cresol, 2,2'-methylenebis(4-methyl-6-tert-butyl-phenol), 1-amino-7-naphthol, p-benzoquinone, 2,6-dichloro-p-benzoquinone, 2-amino-1,4-naphtholquinone, 3-aminoanthraquinone, diphenylamine, p-nitrosodimethylaniline, $\alpha$ and $\beta$-naphthylamine, nitrobenzene, phenothiazine, N-nitrosodimethylamine, hexamethylphosphoramide, n-dodecyl mercaptan, benzenethiol, 2,2-diphenyl-1-picrylhydrazyl (phenyl hydrazine), divinylacetylene, and various antimony and copper salts. Most preferred among the inhibitors are paramethoxyphenol, hydroquinone and its monomethylether, phenothiazine and nitrobenzene. The inhibitors should be added to the reaction mixture in the range of about 50-1000 parts per million parts, by weight, of reactant. preferably about 100-400 ppm.

The esterification itself is carried out by mixing at least about 1 mole of acrylic or methacrylic acid with each mole of the cyclic alcohol, preferably at least about 1.5 moles of acid for each mole of alcohol. The reactants are then heated to reaction temperatures as high as 200° C. and held until the theoretical water of reaction has been removed. A reflux azeotrope solvent in the desired boiling range may be used to aid in water removal. Examples of such solvents, include benzene, toluene, xylene, etc.

Following esterification, the products of the instant invention may be purified by common purification methods, including solvent washing, solvent extraction drying, evaporation, and distillation.

As previously set out, the compositions of the instant invention are useful in practically any end use where vinyl polymerizable monomers are utilized. In addition, they are particularly useful as diluents in unsaturation-containing coatings, particularly as diluents in ultraviolet curable coating compositions.

In the following examples, all parts and percentages are by weight, unless otherwise specified.

EXAMPLE 1.

Into a reactor equipped with a mechanical agitator, reflux condenser with Dean Stark Trap, sampling device and thermometer, were added 400 gms of trimethylolpropane, 243.2 gms of 37 percent, by weight, aqueous formaldehyde, 18 gms of paratoluene sulfonic acid and 3 liters of benzene. The contents were refluxed at about 100° C. until about 209 gms of water were removed. The reaction mixture was then cooled and extracted with three 100 ml. parts of 30 percent aqueous formate to remove the catalyst. The resulting organic layer was dried over magnesium sulfate and the solvent stripped on a rotofilm evaporator to remove the benzene. The crude material was distilled under vacuum and there resulted 381 gms (87 percent by weight yield) of the cyclic formal (bp 110-120° C., 3mm/Hg.).

73 g. of the resulting product were mixed with 40 g. of acrylic acid, 150 ml. of benzene, 10 g. of Amberlyst 15 ion exchange catalyst, available from the Rohm and Haas Corporation, having a hydrogen equivalent weight of 204.1 g./eq. and prepared based upon styrene sulfonic acid and divinyl benzene, 0.0109 g. of phenothiazine, and 0.0109 g. of nitrobenzene. The above-identified constituents were mixed in a three-necked reactor having a mechanical agitator, nitrogen sparge, condenser and Dean Stark trap, and the contents were heated to 90° C. Approximately 7 g. of water were removed over 6-8 hours. The solution was then cooled and filtered, and the excess acrylic acid and benzene were stripped under vacuum. The resulting mixture was then stirred for 15 minutes with 2 g. of activated charcoal and filtered. Analysis of the resulting product indicated that 90% of the reactants had been converted to cyclic formal acrylate.

EXAMPLE 2.

Into the reactor equipped as in Example 1, were added 268 g. of trimethylolpropane, 144 g. of nbutyraldehyde, 500 ml. of benzene, and 41.2 g. of Amberlyst 15 ion exchange catalyst. Utilizing a nitrogen sparge, the contents of the flask were heated to 90° C. and held until 36.3 ml. of water were removed over a four-hour period. The mixture was then cooled and 0.041 g. of phenothiazine, 0.041 g. of nitrobenzene, and 185.4 g. of acrylic acid were added to the reactor. The contents were heated gradually to about 85° C. After 36 ml. of water had been removed, the mixture was filtered and the benzene stripped under vacuum which afforded 461 g. of the corresponding butyral.

EXAMPLE 3.

Example 1 was repeated except that glycerin was used in the place of trimethylolpropane. A product which was 50 percent of the 1,2-cyclic acetal and 50 percent of the 1,3-cyclic acetal resulted.

What is claimed is:

1. A new composition of matter comprising:

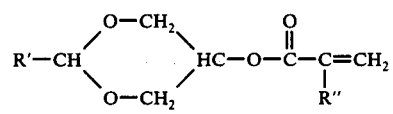

wherein R' is hydrogen, $C_1$-$C_3$ alkyl or $C_1$-$C_3$ halogenated alkyl, and R'' is hydrogen or methyl.

2. A process for preparing the composition of claim 1 which comprises:
    a. reacting an aldehyde having the general formula

R'-CHO wherein R' is hydrogen, $C_1$-$C_3$ alkyl, or $C_1$-$C_3$ halogenated alkyl, with glycerine, at temperatures up to 150° C., and
    b. esterifying the resulting product with acrylic acid or methacrylic acid at temperatures up to about 200° C.

3. The process of claim 2 wherein the aldehyde is a formaldehyde solution and the acid is acrylic acid.

4. The process of claim 2 wherein an alpha beta ethylenically unsaturated vinyl polymerization inhibitor is utilized at about the 50-1000 ppm level in the esterification step.

5. The process of claim 2 wherein the aldehydetriol reaction is catalyzed utilizing an acid catalyst.

* * * * *